United States Patent [19]

Hussey

[11] Patent Number: 4,801,200
[45] Date of Patent: Jan. 31, 1989

[54] OPTOMETRIC LENS TRIAL FRAME

[76] Inventor: Eric S. Hussey, N. 10511 Middleton, Spokane, Wash. 99218

[21] Appl. No.: 30,629

[22] Filed: Mar. 27, 1987

[51] Int. Cl.$^4$ ............................................. A61B 3/04
[52] U.S. Cl. .................................... 351/230; 351/227
[58] Field of Search .............. 351/227, 228, 229, 230, 351/231; 2/452

[56] References Cited

U.S. PATENT DOCUMENTS

| 1,266,224 | 5/1918 | Day | 351/229 |
| 1,962,800 | 6/1934 | Aspenleiter | 351/229 |
| 2,603,785 | 7/1952 | Splaine | 2/452 |

Primary Examiner—Rodney B. Bovernick
Assistant Examiner—Jay Ryan
Attorney, Agent, or Firm—Keith S. Bergman

[57] ABSTRACT

A trial frame is disclosed presenting pairs of lens holders on one or both sides of a common beam for ocular therapy and testing by a plurality of test lenses. Each lens frame holder is grooved to simultaneously accommodate plural lenses and may completely or partially encircle lenses to releasably hold them. Secured at each lateral extremity of the common beam is an elastic head band to quickly and securely position the test frame for use especially as on an active younger child.

6 Claims, 1 Drawing Sheet

OPTOMETRIC LENS TRIAL FRAME

BACKGROUND OF THE INVENTION

1. Related Applications

There are no applications for patent relating hereto heretofore filed in this or any foreign country.

2. Field of the Invention

My invention relates generally to optometric lens test frames and particuarly to a frame quickly securable by a head band to enable use on active younger children.

3. Background and Description of Prior Art

Optometric lens trial frames are well established in the prior art to correct and treat various eye disorders.

Due to the complexity of eye focusing maladies that are common in humans, a variety of lenses of different focal length and type must be available and utilized in a trail apparatus. For example, a focusing defect known as astignatism in which a refracting surface of an eye has unequal curvature, requires a particular lens curvature for correction. Lenses are employed using a combination of spherical and cylindrical curvature so that a remedial spectacle lens and the eye lens in combination achieve a correct focusing. Asymmetrical and prismatic lenses have been developed to correct visual abnormalities and with their use it is critical that these lenses be accurately positionable within a trial lens structure. Focusing problems may include not only those problems associated with a human lens but also an inability of a human eye's associated muscle structure to manipulate the lens to control focusing in the eye or its axial direction. These problems, exemplified by a lazy eye syndrome, require particular lens constructions to retrain and strengthen problem eye muscles.

It is important in optometric therapy that a chosen focal distance and orientation of trial lenses relative to a human eye be constantly maintained to accurately determine the appropriateness and effectiveness of lenses used. During focusing tests many different individual lenses and combinations may be utilized to determine what lens construction is most advantageous for a particular patient involved.

Various devices have in the past been developed to provide a fixed orientation of trial lens apparatus relative to human eyes. Such devices have often provided bulky self-supporting structures developed with complex mountings to accommodate a plurality of lenses in either single or dual frame constructions. There have been helmet constructions to position lenses with various lateral and vertical structural elements to properly orient the trial lenses. These have been structurally associated by means of elaborate linkages and pivots to accommodate various head shapes that are found in humans. Adding to the fitting complexity is the problem of heads shaped in a myriad of configurational combinations including sloping, receding foreheads associated with varying oblong, round and ovoid shapes of cranial structures that create an inordinately large potential combination of heads to be accommodated. As a result, devices of the past have often been deficient in providing comfort while simultaneously effecting the critically accurate positioning of lenses to be tested or utilized in therapy.

Problems associated with prior art lens testing devices are magnified when applied to particular groups of patients. Particularly when children are tested or treated added factors enter the procedure, and when considering the large number of young children in modern society needing corrective lenses, they require particular accommodation. Children are very active their patience and attention span, relative to adults, is limited. Accordingly they do not, in many instances, serenely accept being subjected to the typical bulky and complex structures associated with lens testing and treatment devices. To complicate the procedures even further, children's imaginations are normally very active and therefore awkward and complex trial lens devices often associated with a testing or treatment procedure may appear ominous to a young child and even prevent a proper diagnosis, evaluation or treatment of a child's optical requirements. Since a child's first impression of what he might have to undergo to achieve a proper optical correction is important, confrontation with an unwiedly test apparatus may prevent a child not only from being properly fitted but also, even if fitted, from being amenable to wearing the product emanating from an unpleasant experience.

A significant feature of my invention is the use of my optical test frame on children to allow use of various prescription lenses are required for exercising eyes and correcting maladies associated with eye muscle coordination. Even considering the active nature of children, as noted, the optical test frame apparatus may be worn comfortably for periods of time and a child will not be prone to remove, disturb or shift the test lens apparatus. The apparatus is light weight and accordingly exercise to treat an eye malady may be performed in an efficient and comfortable manner. Furthermore with the multiple lens holding feature of the invention, different refractive lens combinations may be presented to a child's eyes to assist and enhance the corrective procedure.

The willingness of a child to accept my improved test frame device will expedite its use in corrective activities required to strengthen and exercise particular eye muscles and functions. Particularly my test frame has proven to be valuable in treating eye disorders such as strabismias, the common cross-eye syndrome where the eyes will not align and focus properly, amblyopia where one eye will focus and the other is inhibited, and even ocular suppresseion that has its psychological basis in mis-controlling eye muscles to avoid diplopia, a double vision.

The instant invention is distinguished from the prior art not in any one of these features per se, but rather in the combination of all of them to synergistically provide the unique functions necessarily flowing therefrom.

SUMMARY OF THE INVENTION

The present invention provides a light weight, versatile and compact optical test frame that maintains trial lenses at stable and fixed positions relative to the lens of human eyes.

My invention comprises a central horizontal bar with sets of pairs of lens holders symmetrically arranged and formed integrally to said bar on either side to maintain precise alignment.

One set of lens holders is formed with flexible fingers that circumferentially grip lenses to be tested about major portion of their periphery, to allow quick interchangability. The other set of lens holders completely encircle lens to more securely hold lens, and particularly non-symmetrically ground lenses, in fixed angular positions.

The test frame provides layered construction with test frames mechanically secured together to form lens holders for two or more lenses in axial alignment to enable use of combinations of various lenses.

Secured at the lateral extremities of the horizontal bar is an elastic band adjustable to accommodate various head shapes that will be encountered.

My test frame with such a band is pivotal about the horizontal bar and therefore does not have to be removed from a user to quickly present alternate optical refractions from lenses on both sides to a patient.

In creating such a device, it is:

A principal object of my invention to provide a patient supported, light-weight and durable optometric test frame especially adapted for use on children.

A further object of my invention to create an optometric test frame that releasably secures multiple sets of optically refractory lenses for use on a patient.

Another object of my invention to provide an optometric test frame with an elastic head band to securely but comfortably position the test frame during use.

Yet another object of my invention to provide such a test frame that is pivotal about its central bar to enable the presentation of two sets of pairs of refractory lenses to a user without removal of the device from the user.

A still further object of my invention to provide such a device that is of new and novel design, of rugged and durable nature, of simple and economic manufacture, and one otherwise well suited to the uses and purposes of which it is intended.

Other and further objects of my invention will appear from the following specification and accompanying drawings which form a part hereof. In carrying out the objects of my invention, however, it is to be understood that its essential features are susceptible of change in design and structural arrangement with only one practical and preferred embodiment being illustrated in the accompanying drawings as is required.

BRIEF DESCRIPTION OF DRAWINGS

In the accompanying drawings which form a part hereof and wherein like numbers of reference refer to smaller parts throughout.

DESCRIPTION OF THE PREFERRED EMBODIMENT

My inventioon comprises generally lens frame holder 10 supportable and securable about the head of the patient by elastic head band 20.

Figure 1:
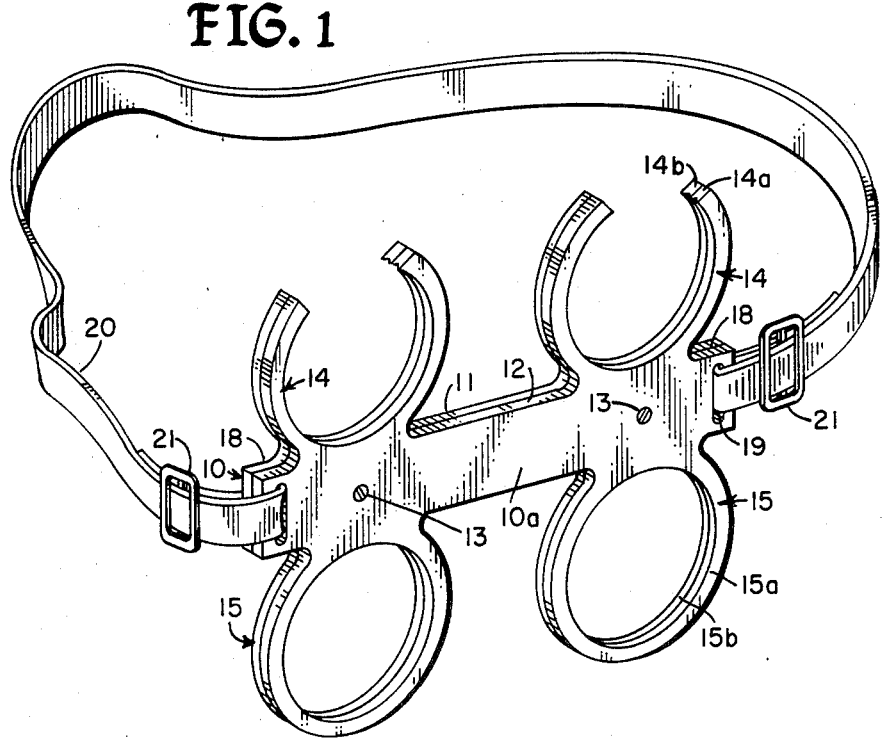
FIG. 1 is an isometric view of my invention showing its various parts, their configuration and relationship.
Figure 2:
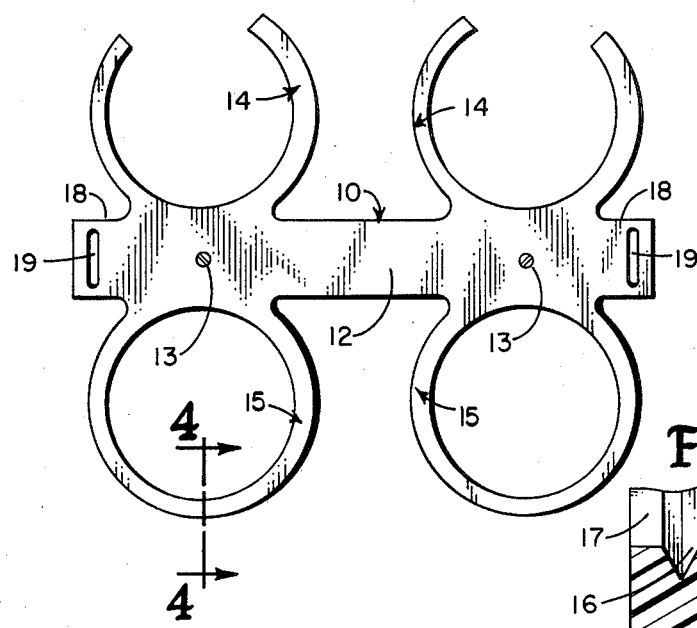
FIG. 2 is an orthographic frontal view of the device of FIG. 1.
Figure 3:
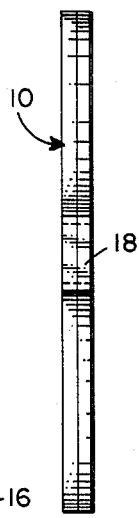
FIG. 3 is an orthographic side view of the device of FIG. 1.

The lens frame holder may be formed of unitary construction or, as shown in FIG. 1, of two similar frame halves 11 and 12 secured together by the assembly fasteners 13. The use of assembled frame halves allows the association of two lens frame holders to accommodate two lenses in an axially aligned array. Conventional fasteners 13, such as rivets, may be utilized for the assembly of the frame halves, or adhesives may be used to bond the frame halves together.

As illustrated, upper lens holder members 14 are formed of flexible, partially encircling finger elements 14a and 14b providing peripheral lens contact over an angle greater than 180 degrees and less than 360 degrees to removably, yet firmly, secure lenses. Lower lens holder members 15 are formed of completely encircling frame elements 15a and 15b that are inserted in a conventional heated optical bath to thermally expand them and allow for the insertion of lenses that are securely and non-rotatably positioned as the lens holders cool and shrink. Accordingly a lens holder depicted by numeral 14 may carry a symmetrically ground lens and may be associated with encircling lens holder 15 where a prismatic lens, for example, may be held in a completely nonslip arrangement.

Lens frame holder 10 is symmetrically formed about an axis extending medially lengthwise of central longitudinal support 10a. Such symmetry enables respective finger elements 14a and 14b to be paired with respective encircling elements 15a and 15b upon rotation of frame half 12, 180 degrees relative to frame half 11. Mechanical joining by fasteners 13 enables such reorientation of frame halves 11 and 12 after disassembly providing additional user flexibility in lens selection.

Figure 4:
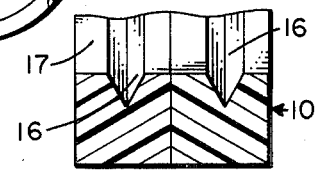
FIG. 4 is a somewhat enlarged, orthographic, cross-sectional view through the lens holder of FIG. 2, taken on the line 4—4 thereon in the direction indicated by the arrows.

The assembled frame halves have formed within the lens holder's inner peripheral surface at least two grooves per assembled lens holder 14, 15 as depicted by numeral 16 in the illustration of FIG. 4. These grooves are bounded by ridges 17 whereby at least two lenses may be secured in axial alignment in each lens holder to provide greater refractive power or refinement or modification as desired by a practitioner. Additional grooves (not shown) may be provided to hold additional lens, but this in general is not necessary in ordinary optometric practice.

Distal ends 18 of lens frame 10 define slots 19 to accommodate loop ends of elastic head band 20. These loop ends are adjustably secured by conventional friction clasps 21. From a single adjustment, band 20 may accommodate a variety of head shapes without additional adjustment, by reason of its elastic deformability. The head band itself is formed of commercially available elastomeric material suitable for such purposes. Alternatives, other than slots 19, may be utilized by one skilled in the art to attach elastic head band 20 to the test frame. Various mechanical connecftions and pivots may be used for economy and expediency, as well as other fasteners that efficient manufacture may dictate.

In use the test frame apparatus is secured about the head of the patient, generally after the proper combination of lenses is inserted within the various lens holders. As may become necessary the head band may be adjusted by manipulation of clasps 21.

When the test frame is used for therapeutic purposes, the lens holder is used for a period of time during which a patient exercises his eyes. If asymmetric lenses be used for therapy, the lower lens holders are most appropriate. To access them lens frame 10 may be pivoted about the distal looped ends of the head-band without removal from a patient's head for subsequent use of the completely encircling lens holders. A similar procedure is utilized when the test frame holder is again used for comparative refractive testing by a practitioner to ascertain the optimum prescriptions among various lens. The flexible fingers of lens holders 14 enable rapid changing of lenses without removal from the wearer's head, to advance a testing procedure without unduly taxing the wearer's patience or comfort.

The foregoing description of my invention is necessarily of a detailed nature so that a specific embodiment of it might be set forth as required, but it is to be understood that various modifications of detail, rearrangement and multiplication of parts might resorted to without departing from its spirit, essence or scope.

Having thusly described my invention, what I desire to protect by Letters Patent, and what I claim is:

1. In a test frame for optometric therapy and testing, that is secured to a wearer's head, and has
   a rigid central longitudinal support, first and second pairs of lens holder members secured to opposite sides of said central support, each member of a lens holder pair positioned on the same side of said support, said support being formed with distal ends including attachment means, and
   a resilient head band, for fastening about a wearer's head, secured to the attachment means of the longitudinal support for enabling rotary motion of the test frame about the support without removal from the wearer's head, the invention comprising:
   the test frame being formed of a plurality of frame halves each half formed with two pairs of lens holder elements with fastening means to secure said frame halves together to form said pairs of lens holder members.

2. An optical test frame as set forth in claim 1 wherein said central longitudinal support's attachment means includes a slot defined inwardly adjacent each distal end of the support to enable the resilient head band to be secured and attached therethrough.

3. An optical test frame as set forth in claim 2 and wherein
   one of said pairs of lens holders members is comprised of a plurality of resilient arcuate finger elements of less than 360 degrees of arc and wherein the other of said pairs of lens holder members is comprised of a plurality of encircling ring elements of 360 degrees of arc, and
   at least said encircling ring elements are formed of material manipulable when heated by immersion in a suitable heated bath material to enable insertion of lenses therein.

4. An optical test frame as set forth in claim 2 wherein each lens holder member is comprised of a resilient arcuate finger element of more than 180 degrees and less than 360 degrees of arc associated with an encircling ring element of 360 degrees of arc.

5. An optical test frame as set forth in claim 2 where said lens holder members are each formed with an internal peripheral surface of alternating ridges and grooves to accommodate the secure positioning of lenses.

6. A test frame for optometric therapy and testing, when secured to a wearer's head, comprising in combination:
   a rigid central longitudinal support, first and second pairs of lens holder members secured to opposite sides of said central support, each member of a lens holder pair positioned on the same side of said support, said support formed with distal ends including attachment means, and said test frame formed of a plurality of frame halves each half formed with two pairs of lens holder elements and fastening means to secure said frame halves together to form said pairs of lens holder members; and
   a resilient head band for fastening about a wearer's head secured to the attachment means of the longitudinal support to enable rotary motion of the test frame about the support without removal from the wearer's head.

* * * * *